United States Patent [19]

Lentz et al.

[11] Patent Number: 4,507,493

[45] Date of Patent: Mar. 26, 1985

[54] CARBONYLATION PROCESS FOR THE PRODUCTION OF AROMATIC ACIDS AND DERIVATIVES THEREOF

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 628,351

[22] Filed: Jul. 6, 1984

[51] Int. Cl.$^3$ ............................................. C07C 69/76
[52] U.S. Cl. ..................... 560/103; 560/100; 560/105; 562/406; 564/180; 564/183; 564/166; 568/38; 546/298; 549/71; 549/72; 549/505; 549/506
[58] Field of Search .................. 560/103, 100, 105; 562/406; 564/180, 183, 166; 568/38; 546/298; 549/71, 72, 505, 506

[56] References Cited

U.S. PATENT DOCUMENTS

| | | | |
|---|---|---|---|
| 3,700,729 | 10/1971 | Fenton | 562/406 |
| 3,769,326 | 10/1973 | Paulik et al. | 562/406 |
| 3,887,595 | 6/1975 | Nozaki | 562/406 |
| 3,965,132 | 6/1976 | Norell | 562/406 |

FOREIGN PATENT DOCUMENTS

EP-82633 10/1983 European Pat. Off. ............ 502/406

*Primary Examiner*—Paul J. Killos
*Attorney, Agent, or Firm*—Clyde L. Tootle; David E. Cotey; J. Frederick Thomsen

[57] ABSTRACT

The present invention provides a process for the preparation of aryl carboxylic acids and derivatives thereof by the carbonylation of aryl sulfonyl chlorides. The aryl sulfonyl chlorides are reacted with carbon monoxide and water or an alcohol or amine in the presence of a zero-valent metal catalyst consisting essentially of palladium.

11 Claims, No Drawings

CARBONYLATION PROCESS FOR THE PRODUCTION OF AROMATIC ACIDS AND DERIVATIVES THEREOF

DESCRIPTION

The present invention provides a novel catalytic carbonylation process for the production of aromatic acids, esters, and/or amides. The novel process involves the carbonylation of an aryl sulfonyl chloride in the presence of water, an alcohol, or an amine and a specified transition metal catalyst.

The preparation of carboxylic acid esters from organic halides by a carbonylation process has been described in U.S. Pat. No. 3,988,358. ("the Heck process"). In the disclosed process, carboxylic acid esters or amides are obtained from aryl halides and substituted derivatives thereof by the reaction of the chosen starting material with an alcohol or primary or secondary amine and carbon monoxide in the presence of a palladium catalyst. A typical example is the conversion of bromobenzene to n-butyl benzoate at 100° C. an one atmosphere of carbon monoxide in the presence of tri-n-butyl amine and a catalytic amount of $PdBr_2[P(C_6H_5)_3]_2$. This reaction does not involve the use of an aryl sulfonyl chloride as the starting material.

It also is known that diaryliodonium salts can be carbonylated to aromatic esters and amides in the presence of a metal catalyst. Specific metals which have been employed include palladium, rhodium, ruthenium, and molybdenum. See, for example, Nippon Kagaku Kaishi, 1982, No. 2, pp. 236-241. Again, the carbonylation of an aryl sulfonyl chloride is not disclosed.

In contrast to the above-described processes, it has now been found that aryl sulfonyl chlorides can be carbonylated to desired aromatic acids or derivatives thereof in the presence of a specified catalytic species. This process thus provides a new and unique method for the replacement of a sulfur moiety with carbon. This transformation has practical applications in the preparation of polyesters and photographic intermediates.

SUMMARY OF THE INVENTION

The present invention provides a process for the preparation of compounds of the formula

wherein R represents H or an aliphatic moiety having up to about 12 carbon atoms and wherein R' represents an aliphatic moiety having up to about 12 carbon atoms. The process comprises reacting an aryl sulfonyl chloride of the formula $ArSO_2Cl$ wherein Ar represents a carbocyclic or heterocyclic aromatic moiety having about 5 to about 20 atoms in the ring or rings thereof, with carbon monoxide and water or an aliphatic alcohol or primary amine having up to about 12 carbon atoms in the presence of a zero-valent metal catalyst consisting essentially of palladium.

DETAILED DESCRIPTION OF THE INVENTION

The present invention relates to the production of aromatic carboxylic acids, esters, and/or amides by a process which involves the carbonylation of an aryl sulfonyl chloride in the presence of a zero-valent metal catalyst consisting essentially of palladium.

The aryl sulfonyl chloride employed as a starting material in the process of the present invention has the following chemical formula:

$ArSO_2Cl$ 

In the above formula, Ar represents a carbocyclic or heterocyclic aromatic moiety having about 5 to about 20 atoms in the ring or rings thereof. Such moieties can be derived from, for example, toluene, benzene, naphthalene, pyridine, thiophene, pyrrole, etc.

The aromatic moiety of the aryl sulfonyl chloride can be substituted or unsubstituted. When substituted, typical substituents include the halides, alkyl groups having up to about 12 carbon atoms, vinyl, carboxylic acid moieties, carboxylic ester moieties, ether groups, nitro groups, etc.

Thus, examples of the aryl sulfonyl chloride include benzenesulfonyl chloride, p-toluenesulfonyl chloride, p-nitrobenzenesulfonyl chloride, p-methoxybenzenesulfonyl chloride, p-isopropylbenzenesulfonyl chloride, p-2-ethylhexylbenzenesulfonyl chloride, etc.

The preparation of aryl sulfonyl chlorides is well known in the art. See, for example, *Organic Chemistry* by R. T. Morrison and R. N. Boyd (Second Edition), pp. 706-07, the teachings of which are incorporated herein by reference.

In accordance with the process of the present invention, an aryl sulfonyl chloride, as described above, is reacted with water or an aliphatic alcohol or primary amine having up to about 12 carbon atoms. In the case where water is employed as a reactant, an aromatic carboxylic acid is produced; when an alcohol is employed, the corresponding aromatic ester is produced; and when an amine is employed, the corresponding amide is produced.

In especially preferred embodiments of the present invention, aromatic esters are produced by the reaction of an aryl sulfonyl chloride with an alcohol as described above. The aliphatic alcohol which is employed in the present process may be monofunctional or multifunctional. Thus, glycols and other polyols are suitable, as are glycol esters, glycol ethers, and other such derivatives. Preferably, the alcohol comprises a lower alkanol (i.e., an alkanol having up to about 12 carbon atoms), ethylene glycol, propylene glycol, neopentyl glycol, ethylene glycol monoacetate, mixtures thereof, etc.

Suitable primary amines which may be employed in the preparation of amides by the process of the present invention include both aliphatic amines and aromatic amines. Suitable primary aliphatic amines include those having up to about 12 carbon atoms, such as monoethylamine, mono-n-butylamine, mono-2-ethylhexylamine, octylamine, dodecylamine, etc. Suitable aromatic amines include aniline, substituted anilines, etc. Multifunctional primary amines, such as the phenylenediamines, also may be used in the present process.

The reaction system of the present process further comprises a zero-valent metal catalyst. The catalyst consists essentially of palladium.

The active metal species is the zero-valent form of the metal. Therefore, in preferred embodiments, the catalyst is provided to the reaction system in the zero-valent form of the metal. More preferably, the zero-valent metal is supported on a suitable material. For example, a highly desirable catalyst material comprises 5% palladium on a carbon support. Of course, other zero-valent catalyst forms can be employed.

The catalyst metal may also be provided in a higher valence state, provided that an in situ reduction to the zero-valent form occurs. Thus, palladium salts, such as palladium acetate, palladium chloride, etc., are also suitable catalyst materials.

The catalyst is present in a concentration of at least about 0.01 millimole per mole of aryl sulfonyl chloride (preferably, about 0.1 to 1 millimole per mole).

The catalytic carbonylation reaction of the present invention is conducted in the presence of carbon monoxide, which is employed in amounts such that the total reaction pressure is in the range of atmospheric to about 500 psig. Superatmospheric pressure may be advantageous when a volatile reactant is employed or when an increase in the rate of reaction is desirable. Thus, reaction pressures from atmospheric pressure up to about 500 psig (about 3500 kPa) are suitable, with pressures from atmospheric pressure up to about 100 psig (about 800 kPa) being preferred.

The process of the present invention can be conducted at room temperature or at elevated temperatures up to about 150° C. Preferably, the temperature of the reaction is in the range of about 25° to 75° C.

It may be desirable also to include in the reaction system a base having a $pK_a$ greater than that of pyridine. The presence of such a base may aid in the prevention of deactivation of the metal catalyst. When employed, the base is present in an amount of about 1 to 10 equivalents of base per equivalent of sulfonyl chloride. Preferably, about 3 equivalents of base per equivalent of sulfonyl chloride is employed. Preferred bases include trialkylamines (such as triethylamine), sodium carbonate, potassium carbonate, etc.

It has been found that the process of the present invention may further be improved by the use of a triaryl phosphine. When present, the triaryl phosphine can be present in a concentration of about 0.1 to 10 moles per mole of palladium (preferably, about 1 mole per mole of palladium). Tritolyl phosphine is an especially suitable triaryl phosphine.

Inert coordinating solvents may be employed, but are not necessary. Such solvents may include, for example, tetrahydrofuran, acetonitrile, etc. In those aspects of the present invention wherein aromatic esters are produced by the reaction of an aryl sulfonyl chloride with carbon monoxide and an alcohol, the alcohol can be employed as solvent. Likewise, when preparing amides, the amine can be employed as solvent.

While not wishing to be bound by theoretical considerations, it is believed that the process of the present invention involves the following reaction pathway:

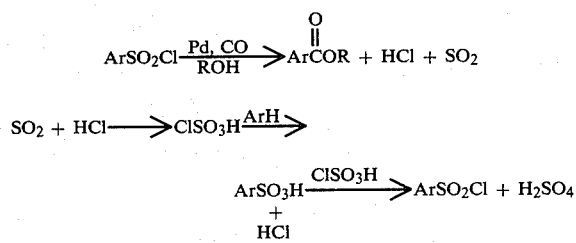

This general procedure can be more specifically exemplified in the case where Ar represents toluene and ROH represents methanol, as follows:

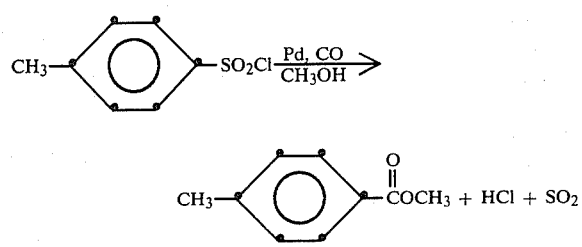

In the above-described reaction scheme, the $SO_2$ and HCl by-products can be removed from the reaction system and then employed in the preparation of the sulfonyl chloride starting material. For example, as shown, the $SO_2$ and HCl by-products can be reacted together to form chlorosulfonic acid, which can then be reacted in excess with the aryl compound so as to form the sulfonyl chloride. Alternatively, the $SO_2$ can be reacted with water to produce sulfuric acid, which can then be reacted with the aryl compound to form the corresponding sulfonic acid. The sulfonic acid can be reacted by known processes (for example, with phosphorus pentachloride or thionyl chloride) so as to produce the desired sulfonyl chloride which is employed as starting material in the present process.

The process of the present invention provides products which are useful as intermediates in the manufacture of photographic chemicals and in the synthesis of polyesters (such as polyethylene terephthalate) and other useful polymeric materials.

The invention will be further illustrated by the following Examples although it will be understood that these Examples are included merely for purposes of illustration and are not intended to limit the scope of the invention.

EXAMPLE 1

This example illustrates the preparation of methyl p-toluate from p-toluenesulfonyl chloride by the process of the present invention.

A 100 ml three-neck, round-bottom flask was fitted with a reflux condenser, a thermometer, mechanical stirrer, and a gas dispersion tube. To the described apparatus were added 0.95 g (5 millimoles) p-toluenesulfonyl chloride, 0.50 g (5 millimoles) of triethylamine, 0.1 g (0.4 millimoles) of palladium acetate, and 40 ml of methanol. Carbon monoxide was bubbled through the reaction mixture while the reaction mixture was heated to reflux (about 60° C.). The resulting mixture was held at reflux for 6 hours. After cooling to 25° C., the reaction mixture was filtered through a Celite pad, and water (200 ml) was added to the filtrate. The aqueous phase was extracted three times with 50 ml of diethyl ether. The ether extracts were combined and dried over magnesium sulfate, and the solvent was removed in vacuo to afford 0.73 g of a light-colored oil which partially solidified into a pale yellow solid. GLPC analysis in comparison with an authentic sample indicated an 83.5% yield of methyl p-toluate.

EXAMPLE 2

Example 1 was repeated, and methyl p-toluate was obtained in an 81% yield.

EXAMPLE 3

Example 1 was repeated except that the reaction mixture was held at reflux for 3 hours. Methyl p-toluate was obtained in a 52% yield.

EXAMPLE 4

Example 3 was repeated except that 0.4 millimole of tritolyl phosphine was added to the reaction mixture. Methyl p-toluate was obtained in a yield of 66%.

EXAMPLE 5

Example 3 was repeated except that benzenesulfonyl chloride was employed instead of p-toluenesulfonyl chloride. Methyl benzoate was obtained in a yield of 66%.

EXAMPLE 6

Example 5 was repeated except that 0.4 millimole of tritolyl phosphine was added to the reaction mixture. Methyl benzoate was obtained in a yield of 79%.

EXAMPLE 7

Example 3 was repeated except that p-methoxybenzenesulfonyl chloride was employed in place of p-toluenesulfonyl chloride. Methyl p-methoxybenzoate was obtained in a yield of 80%.

EXAMPLE 8

Example 7 was repeated except that 0.4 millimole of tritolyl phosphine was added to the reaction mixture. Methyl p-methoxybenzoate was obtained in a yield of 82%.

EXAMPLE 9

Example 3 was repeated except that p-nitrobenzenesulfonyl chloride was employed in place of p-toluenesulfonyl chloride and 0.4 millimole of tritolyl phosphine was employed in the reaction mixture. Methyl p-nitrobenzoate was obtained in a yield of 48%.

The invention has been described in detail with particular reference to preferred embodiments thereof, but it will be understood that variations and modification can be effected within the spirit and scope of the invention.

We claim:

1. A process for the preparation of compounds of the formula

$$\text{ArCOR or ArCNHR}',$$

wherein R represents H or an aliphatic moiety having up to about 12 carbon atoms and R' represents an aliphatic moiety having up to about 12 carbon atoms, said process comprising reacting an aryl sulfonyl chloride of the formula $$\text{ArSO}_2\text{Cl},$$

wherein Ar represents a carbocyclic or heterocyclic aromatic moiety having about 5 to about 20 atoms in the ring or rings thereof, with (i) carbon monoxide and (ii) water or an aliphatic alcohol or primary amine having up to about 12 carbon atoms in the presence of a zero-valent metal catalyst consisting essentially of palladium.

2. The process of claim 1 wherein Ar represents a moiety derived from toluene, benzene, naphthalene, pyridine, thiophene, or pyrrole.

3. The process of claim 1 wherein said alcohol comprises a lower alkanol, ethylene glycol, propylene glycol, neopentyl glycol, ethylene glycol monoacetate, or a mixture thereof.

4. The process of claim 1 wherein the reaction temperature is about 25° to 150° C.

5. The process of claim 1 wherein the reaction system further comprises a base having a $pK_a$ greater than that of pyridine.

6. The process of claim 5 wherein said base comprises triethylamine, sodium carbonate, or potassium carbonate.

7. A process for the preparation of aromatic esters which comprises reacting at a temperature of about 25° to 150° C. an aryl sulfonyl chloride of the formula $$\text{ArSO}_2\text{Cl},$$

wherein Ar represents a moiety derived from toluene, benzene, naphthalene, pyridine, thiophene, or pyrrole, with carbon monoxide and an alcohol comprising a lower alkanol, ethylene glycol, propylene glycol, neopentyl glycol, ethylene glycol monoacetate, or a mixture thereof in the presence of a zero-valent palladium catalyst and a base having a $pK_a$ greater than that of pyridine.

8. The process of claim 7 wherein Ar represents a moiety derived from toluene or benzene.

9. The process of claim 7 wherein said alcohol comprises methanol, ethylene glycol, ethylene glycol monoacetate, or a mixture thereof.

10. The process of claim 7 wherein the reaction temperature is about 25° to 75° C.

11. The process of claim 7 wherein said base comprises triethylamine, sodium carbonate, or potassium carbonate.

* * * * *